United States Patent
Cesa et al.

(10) Patent No.: US 11,737,819 B2
(45) Date of Patent: Aug. 29, 2023

(54) SYSTEM AND METHOD FOR A GRAPHICAL USER INTERFACE THAT PROVIDES IMPROVED CONTROL AND VISUALIZATION FOR AN ABLATION PROCEDURE

(71) Applicant: Avent, Inc., Alpharetta, GA (US)

(72) Inventors: Joseph A. Cesa, Franklin, MA (US); Lisa M. McGregor, Camblee, GA (US); Jennifer J. Barrett, Alpharetta, GA (US); Tyler W. Crone, Atlanta, GA (US); Lee W. Rhein, Hollywood, FL (US); Christopher W. Thurrott, Townsend, MA (US); Morgan Rudolph, Nashua, NH (US); Scott Woodruff, Chicago, IL (US)

(73) Assignee: Avent, Inc., Alpharetta, GA (US)

( * ) Notice: Subject to any disclaimer, the term of this patent is extended or adjusted under 35 U.S.C. 154(b) by 458 days.

(21) Appl. No.: 16/416,371

(22) Filed: May 20, 2019

(65) Prior Publication Data
US 2020/0367963 A1    Nov. 26, 2020

(51) Int. Cl.
*A61B 18/00* (2006.01)
*A61B 18/02* (2006.01)
(Continued)

(52) U.S. Cl.
CPC .......... *A61B 18/1492* (2013.01); *A61B 18/02* (2013.01); *A61B 18/1815* (2013.01);
(Continued)

(58) Field of Classification Search
CPC . A61B 18/1492; A61B 18/02; A61B 18/1815; A61B 18/22; A61B 2018/00434;
(Continued)

(56) References Cited

U.S. PATENT DOCUMENTS 5,334,181 A    8/1994   Rubinsky et al.
5,819,741 A    10/1998  Karlsson et al.
(Continued)

FOREIGN PATENT DOCUMENTS

EP    1 749 492 A1    2/2007
EP    2 942 023 A2    11/2015
(Continued)

OTHER PUBLICATIONS

International Search Report and Written Opinion dated Nov. 4, 2020, from International Application No. PCT/US2020/032647, 19 pages.

*Primary Examiner* — Joseph A Stoklosa
*Assistant Examiner* — Annie L Shoulders
(74) *Attorney, Agent, or Firm* — Meunier Carlin & Curfman LLC

(57) ABSTRACT

A system for delivering energy to a patient's body is disclosed that includes a plurality of probes, a touch-sensitive display screen, and a controller communicatively coupled to each of the probes and the display screen. The controller is configured to perform operations including displaying a virtual control object in the user interface of the touch-sensitive display screen that is associated with an operating parameter of a treatment procedure performed with the probe. The controller is configured to adjust the operating parameter when a user touch action is directed to the virtual control object. The controller is configured to convert the virtual control object into a non-control label based, at least in part, on a current status of the treatment procedure. The controller is configured to prohibit adjustment of the operating parameter using the non-control label in response to a user touch action that is directed to the non-control label.

18 Claims, 10 Drawing Sheets

(51) Int. Cl.
*A61B 18/14* (2006.01)
*A61B 18/18* (2006.01)
*A61B 18/22* (2006.01)

(52) U.S. Cl.
CPC ..... *A61B 18/22* (2013.01); *A61B 2018/00023* (2013.01); *A61B 2018/00434* (2013.01); *A61B 2018/00577* (2013.01); *A61B 2018/00619* (2013.01); *A61B 2018/00791* (2013.01); *A61B 2018/00875* (2013.01); *A61B 2018/0212* (2013.01)

(58) Field of Classification Search
CPC .......... A61B 2018/00577; A61B 2018/00023; A61B 2018/00791; A61B 2018/00875; A61B 2018/0212; A61B 2034/2074; A61B 90/37
See application file for complete search history.

(56) References Cited

U.S. PATENT DOCUMENTS

| | | | |
|---|---|---|---|
| 5,871,481 A | 2/1999 | Kammemberg et al. | |
| 5,954,719 A | 9/1999 | Chen et al. | |
| 6,356,790 B1 | 3/2002 | Maguire et al. | |
| 6,625,482 B1 | 9/2003 | Panescu et al. | |
| 6,679,269 B2 | 1/2004 | Swanson | |
| 7,122,031 B2 | 10/2006 | Edwards et al. | |
| 8,603,087 B2 | 12/2013 | Rubinsky et al. | |
| 8,657,814 B2 | 2/2014 | Werneth et al. | |
| 8,845,630 B2 | 9/2014 | Mehta et al. | |
| 9,005,128 B2 | 4/2015 | Imamura et al. | |
| 9,008,793 B1 | 4/2015 | Cosman, Sr. et al. | |
| 9,308,372 B2 | 4/2016 | Sparks et al. | |
| 9,333,031 B2 | 5/2016 | Salahieh et al. | |
| 9,393,071 B1 | 7/2016 | Boveja et al. | |
| 9,427,284 B2 | 8/2016 | Moss et al. | |
| 9,495,059 B2 | 11/2016 | Shikhman et al. | |
| 9,510,887 B2 | 12/2016 | Burnett et al. | |
| 9,510,909 B2 | 12/2016 | Grant et al. | |
| 9,522,048 B1 | 12/2016 | Schmit et al. | |
| 9,532,831 B2 | 1/2017 | Reinders et al. | |
| 9,547,752 B2 | 1/2017 | Sandhu et al. | |
| 9,592,387 B2 | 3/2017 | Skelton et al. | |
| 9,597,145 B2 | 3/2017 | Nelson et al. | |
| 10,216,985 B2 | 2/2019 | White et al. | |
| 2003/0112390 A1 | 11/2003 | Chen et al. | |
| 2005/0177209 A1 | 8/2005 | Leung et al. | |
| 2005/0177211 A1* | 8/2005 | Leung ................. | A61B 18/148 607/101 |
| 2007/0129633 A1 | 6/2007 | Lee et al. | |
| 2009/0138011 A1 | 5/2009 | Epstein | |
| 2010/0016926 A1 | 1/2010 | Rittman, III | |
| 2011/0172659 A1 | 7/2011 | Brannan | |
| 2012/0209314 A1* | 8/2012 | Weir ..................... | A61B 34/37 606/205 |
| 2012/0260293 A1 | 10/2012 | Young et al. | |
| 2013/0018368 A1 | 1/2013 | Chan et al. | |
| 2013/0030426 A1 | 1/2013 | Gallardo et al. | |
| 2013/0138097 A1 | 5/2013 | Mathur et al. | |
| 2013/0165919 A1 | 6/2013 | Epstein | |
| 2013/0335441 A1 | 12/2013 | Zalev et al. | |
| 2014/0330266 A1 | 11/2014 | Thompson et al. | |
| 2015/0057945 A1 | 2/2015 | White et al. | |
| 2015/0182740 A1 | 7/2015 | Mickelsen | |
| 2015/0297282 A1 | 10/2015 | Cadouri | |
| 2015/0320478 A1* | 11/2015 | Cosman, Jr. .......... | A61B 18/16 606/34 |
| 2015/0320481 A1 | 11/2015 | Cosman, Jr. et al. | |
| 2016/0048635 A1 | 2/2016 | Warner et al. | |
| 2016/0354142 A1 | 12/2016 | Pearson et al. | |
| 2017/0049513 A1 | 2/2017 | Cosman, Jr. et al. | |
| 2017/0065352 A1 | 3/2017 | Razzaque et al. | |
| 2018/0085188 A1 | 3/2018 | Boutoussov et al. | |
| 2018/0110554 A1 | 4/2018 | Zarins et al. | |
| 2018/0206922 A1* | 7/2018 | Wenderow ............ | A61B 34/20 |
| 2019/0083169 A1 | 3/2019 | Single et al. | |
| 2019/0262071 A1* | 8/2019 | Thom ................ | A61B 18/1815 |
| 2019/0269367 A1* | 9/2019 | Reinders ............ | A61N 1/37247 |
| 2020/0015879 A1 | 1/2020 | McGregor et al. | |
| 2020/0085531 A1* | 3/2020 | Harrison ................ | A61B 90/90 |

FOREIGN PATENT DOCUMENTS

| | | |
|---|---|---|
| WO | 2012/129542 | 9/2012 |
| WO | WO 2013/134133 A1 | 9/2013 |
| WO | WO 2014/144359 A1 | 9/2014 |
| WO | WO 2016/090175 A1 | 6/2016 |
| WO | WO 2018/116273 A1 | 6/2018 |
| WO | WO 2018/200254 A2 | 11/2018 |

* cited by examiner

SYSTEM AND METHOD FOR A GRAPHICAL USER INTERFACE THAT PROVIDES IMPROVED CONTROL AND VISUALIZATION FOR AN ABLATION PROCEDURE

FIELD OF THE INVENTION

The present invention relates generally to a system and method for applying energy for the treatment of tissue, and more particularly to a system and method for an improved graphical user interface that provides independent control of multiple radiofrequency probes during an ablation procedure.

BACKGROUND

Lower back injuries and chronic back pain are a major health problem resulting not only in a debilitating condition for the patient, but also in the consumption of a large proportion of funds allocated for health care, social assistance and disability programs. Disc abnormalities and pain may result from trauma, repetitive use in the workplace, metabolic disorders, inherited proclivity, or aging. The existence of adjacent nerve structures and innervation of the disc are very important issues with respect to patient treatment for back pain.

A minimally invasive technique of delivering high-frequency electrical current has been shown to relieve localized pain in many patients. Generally, the high-frequency current used for such procedures is in the radio frequency (RF) range, i.e. between 100 kHz and 1 GHz and more specifically between 300-600 kHz. The RF electrical current is typically delivered from a generator via a plurality of connected electrodes that are placed in a patient's body, in a region of tissue that contains a neural structure suspected of transmitting pain signals to the brain. The electrodes generally include an insulated shaft with an exposed conductive tip to deliver the radio frequency electrical current. Tissue resistance to the current causes heating of tissue adjacent resulting in the coagulation of cells (at a temperature of approximately 45° C. for small unmyelinated nerve structures) and the formation of a lesion that effectively denervates the neural structure in question. Denervation refers to a procedure whereby the ability of a neural structure to transmit signals is affected in some way and usually results in the complete inability of a neural structure to transmit signals, thus removing the pain sensations.

To extend the size of a lesion, radiofrequency treatment may be applied in conjunction with a cooling mechanism, whereby a cooling means is used to reduce the temperature of the tissue near an energy delivery device, allowing a higher voltage to be applied without causing an unwanted increase in local tissue temperature. The application of a higher voltage allows regions of tissue further away from the energy delivery device to reach a temperature at which a lesion can form, thus increasing the size/volume of the lesion.

Such procedures can be done using any suitable number of probes (e.g., from one probe up to four probes), or more, at a time. If one of the probes encounters a condition that causes the probe to stop during its procedure, however, the probe remains inactive until all remaining probes have completed their procedures. Once the other probes have completed their procedures, a user can troubleshoot the problem probe and restart the problem probe's procedure. Unfortunately, such workflow requires the user to waste valuable time waiting for procedures to finish, adding probe procedure times together, which extends the overall time that the patient must endure the treatment procedure.

A graphical user interface can be provided on a display screen to allow the user to control the various procedures. However, the size of the graphical user interface is practically limited by the size of the display screen. For each probe that is communicatively coupled with the controller, multiple pieces of information are often displayed in the graphical user interface. This can lead to visual clutter and inhibit an operator or physician from locating significant data within the interface. Additionally, current interfaces can allow the operator or physician to adjust aspects of the treatment procedures in ways that are unsafe for the patient.

Thus, the present disclosure is directed to systems and methods for an improved graphical user interface that provides independent control of multiple radiofrequency probes during an ablation procedure.

SUMMARY OF THE INVENTION

Objects and advantages of the invention will be set forth in part in the following description, or may be obvious from the description, or may be learned through practice of the invention.

In one aspect, the present disclosure is directed to a system for delivering energy to a patient's body. The system can includes a plurality of probes each having an elongate member with a distal region having an electrically non-conductive outer circumferential portion and a proximal region. Each of the plurality of probes further includes an electrically conductive energy delivery device extending distally from the electrically non-conductive outer circumferential portion for delivering one of electrical and radiofrequency energy to the patient's body. The energy delivery devices further include an electrically conductive outer circumferential surface. The system also includes a touch-sensitive display screen and a controller communicatively coupled to each of the plurality of probes and the touch-sensitive display screen. The controller includes memory and a processor. The memory stores instructions that, when executed by the processor, cause the processor to perform operations including displaying a virtual control object in the user interface of the touch-sensitive display screen. The virtual control object is associated with an operating parameter of a treatment procedure performed by the probe. The operations include detecting a user touch action directed to the virtual control object. The operations include performing a control action associated with the treatment procedure that includes adjusting the operating parameter associated with the virtual control object when the user touch action directed to the virtual control object is detected. The operations include converting the virtual control object into a non-control label based, at least in part, on a current status of the treatment procedure. The controller is configured to prohibit adjustment of the operating parameter using the non-control label in response to a user touch action that is directed to the non-control label.

In a particular embodiment, the virtual control object is converted into the non-control object when adjusting the operating parameter associated with the virtual control object would be unsafe for the patient.

In a particular embodiment, the virtual control object is converted into the non-control object in response to at least one of the treatment procedure being initiated or the time remaining associated with the treatment procedure being less than a predetermined time threshold.

In a particular embodiment, converting the virtual control object into the non-control label includes changing a visual characteristic of the virtual control object. The visual characteristic can include at least one of a color, size, brightness, font, location, or contrast of the virtual control object.

In a particular embodiment, converting the virtual control object into the non-control label includes changing a location of the virtual control object within the user interface.

In a particular embodiment, the controller may be further configured to display a second non-control label in the user interface that is separate from the virtual control object and non-control label. The second non-control label can have a visual characteristic that is distinct from the virtual control object.

In another aspect, the present disclosure is directed to a system for delivering energy to a patient's body. The system includes a plurality of probes each including an elongate member having a distal region with an electrically non-conductive outer circumferential portion and a proximal region. Each of the plurality of probes further includes an electrically conductive energy delivery device extending distally from said electrically non-conductive outer circumferential portion for delivering at least one of electrical or radiofrequency energy to the patient's body and having an electrically conductive outer circumferential surface. The system includes a touch-sensitive display screen and a controller communicatively coupled to each of the plurality of probes and the touch-sensitive display screen. The controller includes memory and a processor. The memory stores instructions that, when executed by the processor, cause the processor to perform operations including determining whether an operating parameter of a treatment procedure that is being performed by at least one of the plurality of probes qualifies as contextually important based, at least in part, on a status of the treatment procedure. The operations include displaying an urgent label within a user interface of the touch-sensitive display that includes real-time values of the operating parameter.

In a particular embodiment, the urgent label includes real-time values of the operating parameter.

In a particular embodiment, the operations can include displaying a non-urgent label that describes the operating parameter when it is determined that the operating parameter does not qualify as contextually important.

In a particular embodiment, the operations can further include displaying a non-urgent label that is separate from the urgent label. The urgent label can have a visual characteristic that is distinct from the non-urgent label. As examples, the visual characteristic can include at least one of size, color, brightness, font, location, or contrast.

In a particular embodiment, the operations can further include converting the urgent label to a non-urgent label when it is determined that the operating parameter no longer qualifies as contextually important based, at least in part, on the current phase of the treatment procedure.

In some embodiments, the operating parameter can include at least one of impedance, time remaining, or temperature at a distal region of the at least one of the plurality of probes. In such embodiments, the operating parameter can qualify as contextually important when the status of the treatment procedure includes actively delivering at least one of electrical and radiofrequency energy to the patient's body.

In another aspect, the present disclosure is directed to a method for delivering energy to a patient's body using a probe. The method includes displaying, by one or more control devices, a virtual control object within a user interface of a touch-sensitive display screen. The virtual control object is associated with an operating parameter of a treatment procedure performed by the probe. The operations include detecting, by the one or more control devices, a user touch action directed to the virtual control object; when the user touch action directed to the virtual control object is detected, performing, by the one or more control devices, a control action associated with the treatment procedure that includes adjusting the operating parameter associated with the virtual control object; and converting, by the one or more control devices, the virtual control object into a non-control label based, at least in part, on a current status of the treatment procedure, wherein the controller is configured to prohibit adjustment of the operating parameter using the non-control label in response to a user touch action that is directed to the non-control label.

In a particular embodiment, the urgent label is visually emphasized with at least one of a color, size, contrast, or brightness, as compared with surrounding portions of the user interface.

In a particular embodiment, the virtual control object is converted into the non-control object when adjusting the operating parameter associated with the virtual control object would be unsafe for the patient.

In a particular embodiment, converting the virtual control object into the non-control label includes changing a visual characteristic of the virtual control object. The visual characteristic can include at least one of a color, size, brightness, font, location, or contrast of the virtual control object.

In a particular embodiment, the controller may be further configured to display a second non-control label in the user interface that is separate from the virtual control object and non-control label. The second non-control label can have a visual characteristic that is distinct from the virtual control object.

These and other features, aspects and advantages of the present invention will become better understood with reference to the following description and appended claims. The accompanying drawings, which are incorporated in and constitute a part of this specification, illustrate embodiments of the invention and, together with the description, explain the principles of the invention.

BRIEF DESCRIPTION OF THE DRAWINGS

A full and enabling disclosure of the present invention, including the best mode thereof, directed to one of ordinary skill in the art, is set forth in the specification, which refers to the appended figures, in which.

DETAILED DESCRIPTION OF THE INVENTION

Figure 1A:
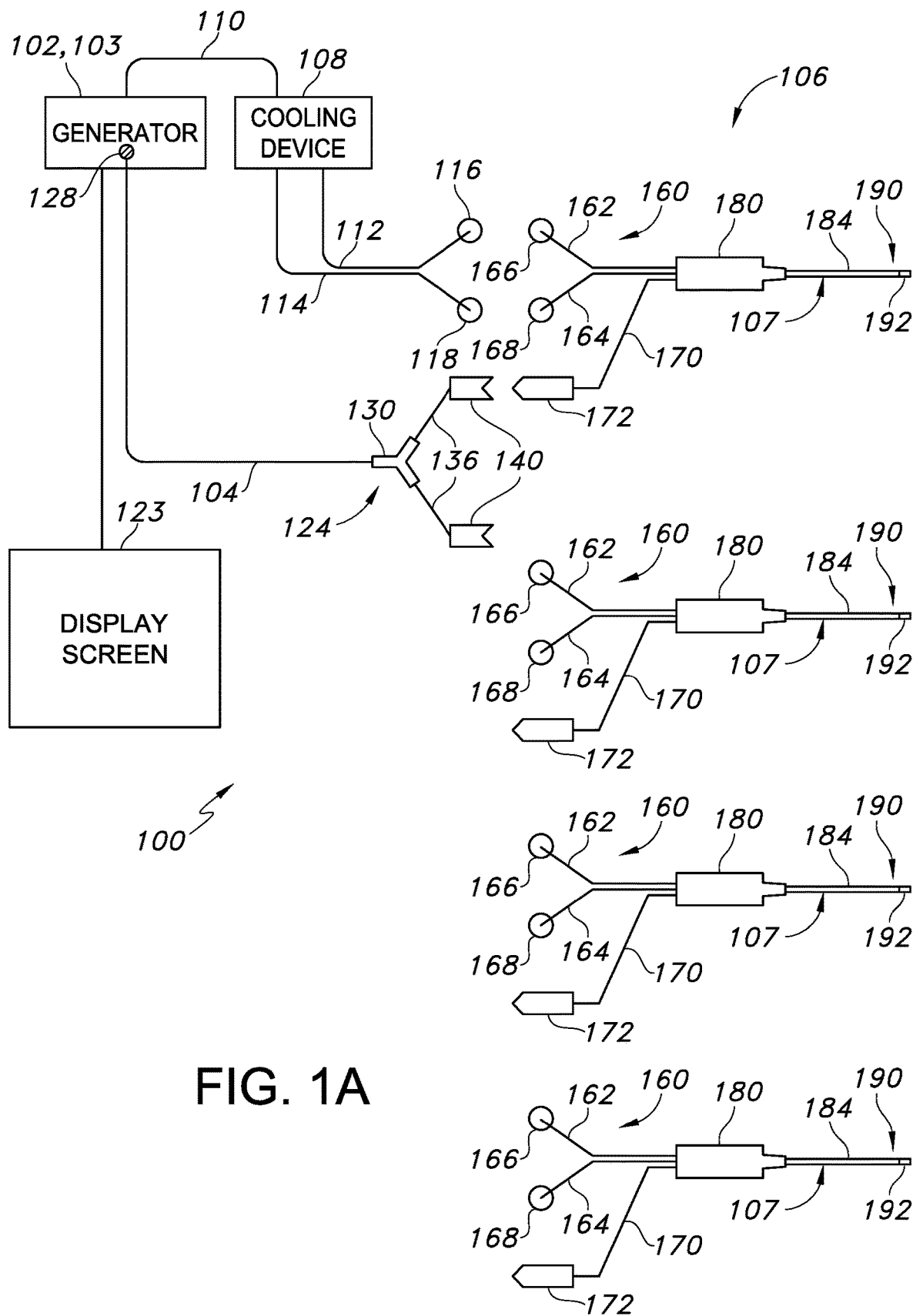
FIG. 1A illustrates a portion of one embodiment of a system for applying radio frequency electrical energy to a patient's body according to the present disclosure.

Reference will now be made in detail to one or more embodiments of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

For the purposes of this invention, a lesion refers to any effect achieved through the application of energy to a tissue in a patient's body, and the invention is not intended to be limited in this regard. Furthermore, for the purposes of this description, proximal generally indicates that portion of a device or system next to or nearer to a user (when the device is in use), while the term distal generally indicates a portion further away from the user (when the device is in use).

According to one aspect of the present disclosure, a controller can be communicatively to a plurality of probes and a touch-sensitive display screen. The controller can be configured to display a user interface on the touch-sensitive display that allows the user to control (e.g., start, stop, adjust) aspects of the treatment procedures performed with the probes. For example, in some embodiments, the controller may display a virtual control object (e.g., a button) that permits control of an operating parameter, such as a target probe temperature. However, it may be disadvantageous to adjust various parameters at different times before or during the treatment procedures. For example, it may be unsafe to adjust a target temperature for the probe tip once the treatment procedure has been started. The controller may be configured to convert virtual control objects into non-control labels based on a current status of the treatment procedure. The controller may be configured to prohibit adjustment of the operating parameter using the non-control label in response to a user touch action that is directed to the non-control label.

For example, when the treatment procedure is initiated, the controller may convert a virtual control object that is configured to adjust the target temperature into a non-control label that displays the target temperature. In another example, the controller may be configured to convert a virtual control object that is configured to stop the treatment procedure into a non-control label when it becomes unsafe for the patient for the treatment procedure to be stopped.

Virtual control objects and non-control labels may have differing visual characteristics such that an operator or physician can easily distinguish the virtual control objects from the non-control labels. Example visual characteristics include color, size, brightness, font, location, or contrast.

In some embodiments, the controller may be configured to display operating parameters to the operator and/or physician in an intelligent manner based on the contextual importance of the respective parameter. The controller can be configured to determine whether a given operating parameter qualifies as contextually important based, at least in part, on a status of the treatment procedure. The controller may display an urgent label that includes real-time values of the operating parameter (e.g., critical values) when it is determined that the operating parameter qualifies as contextually important. For example, the various operating parameters (e.g., current temperature of the probe tip, time remaining) may qualify as contextually important during the treatment procedure, but may not qualify before the treatment procedure is initiated. Thus, the controller may intelligently display real-time values of contextually important operating parameters based on the status of the treatment procedure. The status of the treatment procedure can also include other information, such as the difference between the operating parameter and an associated threshold or critical value. One of ordinary skill in the art would understand that the contextual importance of the operating parameters can depend on a variety of information associated with the status of the treatment procedure.

Urgent labels and non-urgent labels may have differing visual characteristics such that an operator or physician can easily distinguish the urgent labels from the non-urgent labels. Example visual characteristics include color, size, brightness, font, location, or contrast. For instance, urgent labels (e.g., critical values) can be displayed in larger font (e.g., 30 point font or larger) to be legible to a physician who is not directly next to the display screen, for example, standing six feet away or more. The non-urgent labels (e.g., non-critical values) can be displayed in a smaller font (e.g., 10-18 point font or smaller) such that a technician standing close to the display screen (e.g., one to two feet) can read the non-urgent labels. As such, the non-urgent labels can provide information to the technician without adding visual clutter for the physician.

Additionally, in some embodiments, information displayed on the user interface (e.g., urgent labels, non-urgent labels, virtual control objects, non-control objects) may be color coded such that the operator and/or physician can easily classify the information. For example, a plurality of channel control regions can be displayed within the user interface, and each channel control region can correspond with one or more of the plurality of probes. Each channel control region can have an associated color. Information displayed within each channel control region may be displayed in the respective color of each channel control region. However, controls (e.g., virtual control objects) may be displayed in a color that is distinct from the respective colors of the plurality of channel control regions. As an example, four channel control regions may be displayed. Information in a first channel control region may be displayed in orange; information in a second channel control region may be displayed in green; information in a third channel control region may be displayed in blue; and information in a third channel control region may be displayed in purple. However, virtual control objects may be displayed within two or more of the channel control regions in white to visually distinguish the virtual control objects from other portions of the channel control region (e.g., the non-control labels).

In some embodiments, an alarm and/or warning window may be displayed within a channel to indicate an unsatisfactory condition with the associated treatment procedure. For example, the controller may be configured to detect when an operating parameter (e.g., an actual temperature, impedance, power output, etc.) has exceeded a threshold associated with the operating parameter. Depending on the severity of the problem, the controller may automatically stop the treatment procedure and display an alarm or may provide a warning to the user. Such alarms and/or warning may be displayed in a color that is distinct from the colors of the channel control regions. Additionally, the channel control region and/or alarm window may be outlined or emphasized in a color that is distinct from the colors of the channel control regions, such as red or white. The alarm and/or warning may include information displayed in the same color as the outline or another color that is distinct from the colors of the channel control regions, such as yellow. In some embodiments, warnings may include text displayed in one color (e.g., yellow), and alarms may include text displayed in a different color (e.g., white).

In some embodiments, if all channel control regions become inoperative such that energy is not delivered to the plurality of probes, a "global alarm" may be displayed. The global alarm may include a window that is superimposed over two or more of the channel control regions. Two or more of the channel control regions may be darkened (e.g., faded to black) to emphasize the global alarm. The global alarm may include a message displayed in a color that provides a high contrast with a background of the message (e.g., white text over a black background).

Referring now to the drawings, FIG. 1A illustrates a schematic diagram of one embodiment of a system 100 of the present invention. As shown, the system 100 includes a generator 102, a cable 104, at least one probe assembly 106 having a plurality of probes 107, one or more cooling devices 108, a pump cable 110, one or more proximal cooling supply tubes 112 and one or more proximal cooling return tubes 114. As shown in the illustrated embodiment, the generator 102 is a radio frequency (RF) generator, but may optionally be any energy source that may deliver other forms of energy, including but not limited to microwave energy, thermal energy, ultrasound and optical energy. The generator 102 may include or be communicatively coupled with a controller 103 that is operable to communicate with one more devices, for example with the probes 107 and the one or more cooling devices 108. Such communication may be unidirectional or bidirectional depending on the devices used and the procedure performed.

The controller 103 may correspond to any suitable processor-based device(s), such as a computing device or any combination of computing devices. Thus, in several embodiments, the controller 103 may include one or more processor(s) and associated memory device(s) configured to perform a variety of computer-implemented functions. As used herein, the term "processor" refers not only to integrated circuits referred to in the art as being included in a computer, but also refers to a controller, a microcontroller, a microcomputer, a programmable logic controller (PLC), an application specific integrated circuit, and other programmable circuits. Additionally, the memory device(s) of the controller 103 may generally comprise memory element(s) including, but not limited to, computer readable medium (e.g., random access memory (RAM)), computer readable non-volatile medium (e.g., a flash memory), a compact disc-read only memory (CD-ROM), a magneto-optical disk (MOD), a digital versatile disc (DVD) and/or other suitable memory elements. Such memory device(s) may generally be configured to store suitable computer-readable instructions that, when implemented by the processor(s) configure the controller 103 to perform various computer-implemented functions, such as one or more aspects of the methods 800, 900 described below with reference to FIGS. 8 and 9.

In addition, as shown, a distal region 124 of the cable 104 may include a splitter 130 that divides the cable 104 into two distal ends 136 such that the probes 107 can be connected thereto. A proximal end 128 of the cable 104 is connected to the generator 102. This connection can be permanent, whereby, for example, the proximal end 128 of the cable 104 is embedded within the generator 102, or temporary, whereby, for example, the proximal end 128 of cable 104 is connected to generator 102 via an electrical connector. The two distal ends 136 of the cable 104 terminate in connectors 140 operable to couple to the probes 107 and establish an electrical connection between the probes 107 and the generator 102. In alternate embodiments, the system 100 may include a separate cable for each probe assembly 106 being used to couple the probes 107 to the generator 102. Alternatively, the splitter 130 may include more than two distal ends. Such a connector is useful in embodiments having more than two devices connected to the generator 102, for example, if more than two probe assemblies are being used.

Figure 1B:
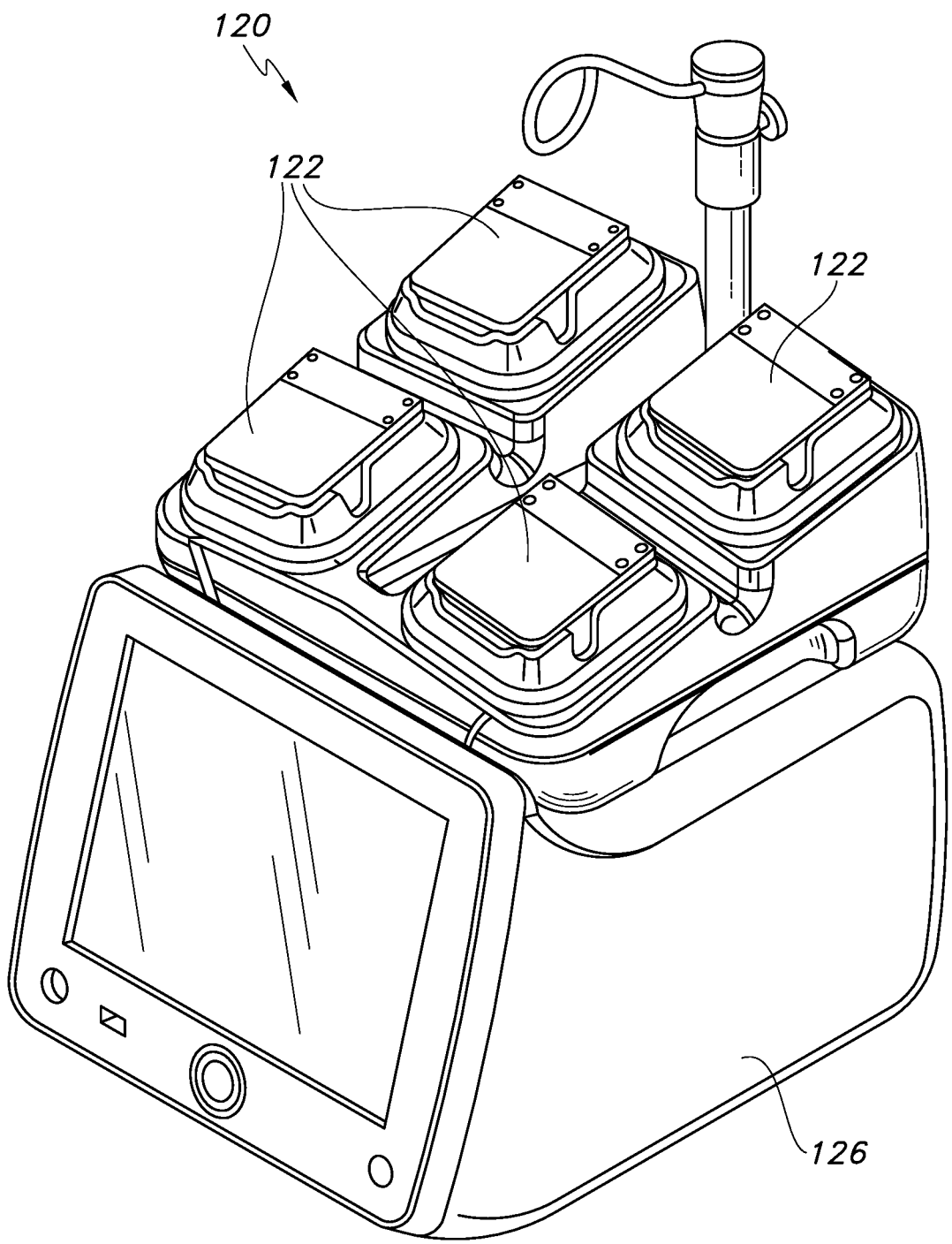
FIG. 1B illustrates a perspective view of one embodiment of a pump assembly according to the present disclosure.

The cooling device(s) 108 may include any means of reducing a temperature of material located at and proximate to one or more of the probes 107. For example, as shown in FIG. 1B, the cooling devices 108 may include a pump assembly 120 having one or more peristaltic pumps 122 operable to circulate a fluid from the cooling devices 108 through one or more proximal cooling supply tubes 112, the probes 107, one or more proximal cooling return tubes 114 and back to the one or more cooling devices 108. For example, as shown, the pump assembly 120 includes four peristaltic pumps 122 coupled to a power supply 126. In alternate embodiments, the pump assembly 120 may include only one peristaltic pump or greater than four pumps. The fluid may be water or any other suitable fluid.

Referring to FIG. 1A, the controller 103 may be communicatively coupled with a display screen 123 (e.g., a touch-sensitive display screen) for displaying a user interface, for example as described below with reference to FIGS. 4 through 9D. The user interface may display various aspects of a treatment procedure, including but not limited to any operating parameters that are relevant to a treatment procedure, such as temperature, impedance, etc. and errors or warnings related to a treatment procedure. The display screen 123 may be responsive to user touch actions directed to the user interface such that the user can adjust one or more individual operating parameters of the various treatment procedures.

The controller 103 may be configured for facilitating communication between the cooling devices 108 and the generator 102. In this way, feedback control is established between the cooling device(s) 108 and the generator 102. The feedback control may include the generator 102, the probes 107 and the cooling devices 108, although any feedback between any two devices is within the scope of the present invention. The feedback control may be implemented, for example, in a control module which may be a component of the generator 102. In such embodiments, the generator 102 is operable to communicate bi-directionally with the probes 107 as well as with the cooling devices 108. In the context of this invention, bi-directional communication refers to the capability of a device to both receive a signal from and send a signal to another device.

As an example, the controller 103 may receive temperature measurements from one or more of the plurality of probes 107. Based on the temperature measurements, the generator 102 may perform some action, such as modulating the power that is sent to the probes 107 (e.g., using one or more control loops). More specifically, aspects of the treatment procedures performed by the various probes 107 may be actively controlled, for example using a control loop (e.g., proportional-integral or proportional-integral-derivative control loop) based on information received by one or more sensors. For example, an amount of energy delivered through the energy delivery devices 192 may be controlled. The flow rate of the peristaltic pumps 122 and resulting cooling may also be actively controlled. In further embodiments, the generator 102 may control the energy delivered to the tissue based on the measured temperature measured by the temperature sensing element(s) 402 (see FIG. 2) and/or impedance sensors. For example, power to each of the probes 107 can be increased when a temperature measurement is low or decreased when a measurement is high. This variation of power may be different for each probe assembly. In some cases, the generator 102 may terminate power to one or more probes 107. Thus, the generator 102 may receive a signal (e.g. temperature measurement) from one or more of probes 107, determine the appropriate action, and send a signal (e.g. decreased or increased power) back to one or more of the probes 107. Alternatively, the generator 102 may send a signal to the cooling devices 108 to either increase or decrease the flow rate or degree of cooling being supplied to one or more of the probes 107.

More specifically, the pumps may communicate a fluid flow rate to the controller 103 and may receive communications from the controller 103 instructing the pumps to modulate this flow rate. In some instances, the peristaltic pumps may respond to the controller 103 by changing the flow rate or turning off for a period of time. With the cooling devices 108 turned off, any temperature sensing elements associated with the probes 107 would not be affected by the cooling fluid allowing a more precise determination of the surrounding tissue temperature to be made. In addition, when using more than one probe assembly 106, the average temperature or a maximum temperature in the temperature sensing elements associated with probes 107 may be used to modulate cooling.

In other embodiments, the cooling devices 108 may reduce the rate of cooling or disengage depending on the distance between the probes 107. For example, when the distance is small enough such that a sufficient current density exists in the region to achieve a desired temperature, little or no cooling may be required. In such an embodiment, energy is preferentially concentrated between the energy delivery devices 192 through a region of tissue to be treated, thereby creating a strip lesion. A strip lesion is characterized by an oblong volume of heated tissue that is formed when an active electrode is near a return electrode of similar dimensions. This occurs because at a given power, the current density is preferentially concentrated between the electrodes and a rise in temperature results from current density.

The cooling devices 108 may also communicate with the controller 103 to alert the controller 103 to one or more possible errors and/or anomalies associated with the cooling devices 108. For example, if cooling flow is impeded or if a lid of one or more of the cooling devices 108 is opened. The controller 103 may then act on the error signal by at least one of alerting a user, aborting the procedure, and modifying an action.

Still referring to FIG. 1A, the proximal cooling supply tubes 112 may include proximal supply tube connectors 116 at the distal ends of the one or more proximal cooling supply tubes 112. Additionally, the proximal cooling return tubes 114 may include proximal return tube connectors 118 at the distal ends of the one or more proximal cooling return tubes 114. In one embodiment, the proximal supply tube connectors 116 are female luer-lock type connectors and the proximal return tube connectors 118 are male luer-lock type connectors although other connector types are intended to be within the scope of the present invention.

In addition, as shown in FIG. 1A, each of the probes 107 may include a proximal region 160, a handle 180, a hollow elongate shaft 184, and a distal tip region 190 that includes the one or more energy delivery devices 192. Further, as shown, the proximal region 160 includes a distal cooling supply tube 162, a distal supply tube connector 166, a distal cooling return tube 164, a distal return tube connector 168, a probe assembly cable 170, and a probe cable connector 172. In such embodiments, the distal cooling supply tube 162 and distal cooling return tube 164 are flexible to allow for greater maneuverability of the probes 107, but alternate embodiments with rigid tubes are possible.

Further, in several embodiments, the distal supply tube connector 166 may be a male luer-lock type connector and the distal return tube connector 168 may be a female luer-lock type connector. Thus, the proximal supply tube connector 116 may be operable to interlock with the distal supply tube connector 166 and the proximal return tube connector 118 may be operable to interlock with the distal return tube connector 168.

The probe cable connector 172 may be located at a proximal end of the probe assembly cable 170 and may be operable to reversibly couple to one of the connectors 140, thus establishing an electrical connection between the controller 103 and the probe assembly 106. The probe assembly cable 170 may include one or more conductors depending on the specific configuration of the probe assembly 106. For example, in one embodiment, the probe assembly cable 170 may include five conductors allowing probe assembly cable 170 to transmit RF current from the controller 103 to the one or more energy delivery devices 192 as well as to connect multiple temperature sensing devices to the controller 103 as discussed below.

The energy delivery devices 192 may include any means of delivering energy to a region of tissue adjacent to the distal tip region 190. For example, the energy delivery devices 192 may include an ultrasonic device, an electrode or any other energy delivery means and the invention is not limited in this regard. Similarly, energy delivered via the energy delivery devices 192 may take several forms including but not limited to thermal energy, ultrasonic energy, radiofrequency energy, microwave energy or any other form of energy. For example, in one embodiment, the energy delivery devices 192 may include an electrode. The active region of the electrode may be 2 to 20 millimeters (mm) in length and energy delivered by the electrode is electrical energy in the form of current in the RF range. The size of the active region of the electrode can be optimized for placement within an intervertebral disc, however, different sizes of active regions, all of which are within the scope of the present invention, may be used depending on the specific procedure being performed. In some embodiments, feedback from the controller 103 may automatically adjust the exposed area of the energy delivery device 192 in response to a given measurement such as impedance or temperature. For example, in one embodiment, the energy delivery devices 192 may maximize energy delivered to the tissue by implementing at least one additional feedback control, such as a rising impedance value.

Figure 2:
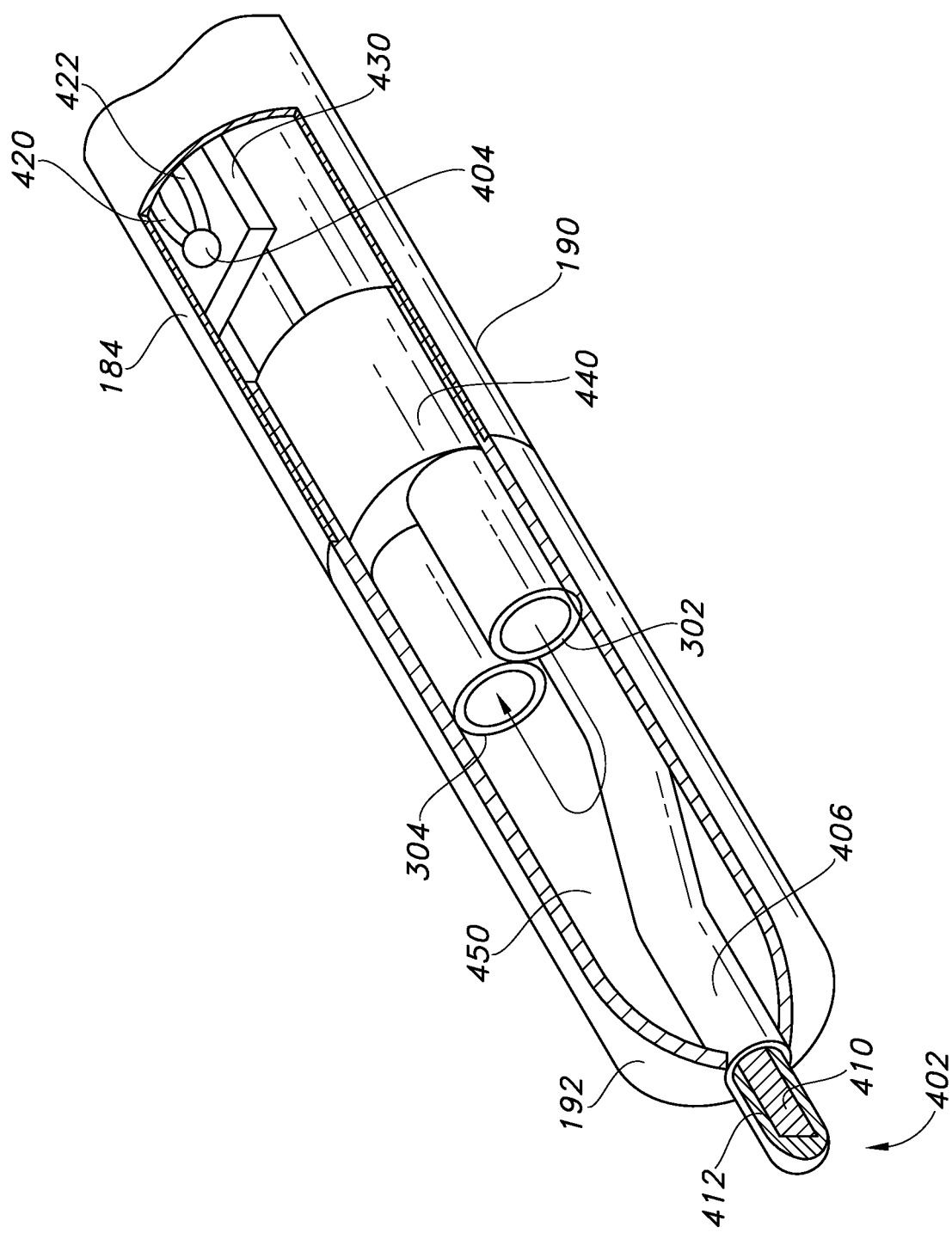
FIG. 2 illustrates a perspective cut-away view of one embodiment of a distal tip region of a probe assembly according to the present disclosure.

Referring in detail to FIG. 2, a perspective cut-away view of one embodiment of the distal tip region 190 of the probe assembly 106 is illustrated. As shown, the distal tip region 190 includes one or more temperature sensing elements 402 which are operable to measure the temperature at and proximate to the one or more energy delivery devices 192. The temperature sensing elements 402 may include one or more thermocouples, thermometers, thermistors, optical fluorescent sensors or any other means of sensing temperature. In one embodiment, the temperature sensing elements 402 are connected to the controller 103 via probe assembly cable 170 and cable 104 although any means of communication between the temperature sensing elements 402 and the controller 103, including wireless protocols, are included within the scope of the present invention. More specifically, as shown, the temperature sensing element(s) 402 may include a thermocouple junction made by joining a stainless steel hypotube 406 to a constantan wire 410, wherein the constantan wire 410 is insulated by insulation 412. In this embodiment, the junction of hypotube 406 and the constantan wire 410 is made by laser welding, although any other means of joining two metals may be used. Furthermore, in this embodiment, the hypotube 406 and the constantan wire 410 extend through a lumen of the elongate shaft 184 and connect to the probe assembly cable 170 within the handle 180.

Further, as shown, the temperature sensing element 402 of each probe 107 protrudes beyond the energy delivery device 192. Placing the temperature sensing elements 402 at this location, rather than within a lumen 450 defined by the energy delivery device 192, is beneficial because it allows the temperature sensing element 402 to provide a more accurate indication of the temperature of tissue proximate to the energy delivery device 192. This is due to the fact that, when extended beyond the energy delivery device 192, the temperature sensing element 402 will not be as affected by the cooling fluid flowing within the lumen 450 as it would be were it located within lumen 450. Thus, in such embodiments, the probe assembly 106 includes a protrusion protruding from the distal region of the probe assembly, whereby the protrusion is a component of the temperature sensing element 402. Referring still to FIG. 2, the probe assembly 106 may further include one or more secondary temperature sensing elements 404 located within the elongate shaft 184 at some distance away from the energy delivery device 192, and positioned adjacent a wall of the elongate shaft 184. The secondary temperature sensing elements 404 may similarly include one or more thermocouples, thermometers, thermistors, optical fluorescent sensors or any other means of sensing temperature. For example, as shown, the secondary temperature sensing element 404 is a thermocouple made by joining copper and constantan thermocouple wires, designated as 420 and 422 respectively. Further, in certain embodiments, the copper and constantan wires 420 and 422 may extend through a lumen of the elongate shaft 184 and may connect to the probe assembly cable 170 within the handle 180.

In addition, the probe assembly 106 may further include a thermal insulator 430 located proximate to any of the temperature sensing elements 402, 404. As such, the thermal insulator 430 may be made from any thermally insulating material, for example silicone, and may be used to insulate any temperature sensing element from other components of the probe assembly 106, so that the temperature sensing element will be able to more accurately measure the temperature of the surrounding tissue. More specifically, as shown, the thermal insulator 430 is used to insulate the temperature sensing element 404 from cooling fluid passing through the shaft supply tube 302 and the shaft return tube 304.

In further embodiments, the probe assembly 106 may also include a radiopaque marker 440 incorporated somewhere along the elongate shaft 184. For example, as shown in FIG. 2, an optimal location for a radiopaque marker may be at or proximate to the distal tip region 190, adjacent the energy delivery device 192. The radiopaque markers are visible on fluoroscopic x-ray images and can be used as visual aids when attempting to place devices accurately within a patient's body. These markers can be made of many different materials, as long as they possess sufficient radiopacity. Suitable materials include, but are not limited to silver, gold, platinum and other high-density metals as well as radiopaque polymeric compounds. Various methods for incorporating radiopaque markers into or onto medical devices may be used, and the present invention is not limited in this regard.

Further, as shown, the elongate shaft 184 and the electrode 192 overlap to secure the electrode in place. In this embodiment, the lumen defined by the elongate shaft 184 and the electrode 192 at this portion of the distal tip region 190 contains a radiopaque marker 440 made of silver solder, which fills the lumen such that any cooling fluid supplied to the probe assembly 106, that is not located within one of the cooling tubes described earlier, is confined to the distal tip region 190 of probe assembly 106. Thus, in such an embodiment, the silver solder may be referred to as a flow impeding structure since it functions to restrict the circulation of fluid to a specific portion (in this case, at least a portion of distal region 190) of the probe assembly 106.

In other words, cooling fluid may flow from the cooling devices 108, through the cooling supply tubes to the distal tip region 190 of the probe assembly 106. The cooling fluid may then circulate within the lumen 450 defined by the electrode 192 to provide cooling thereto. As such, the internally-cooled probe as described herein is defined as a probe having such a configuration, whereby a cooling medium does not exit probe assembly 106 from a distal region of probe assembly 106. The cooling fluid may not circulate further down the elongate shaft 184 due to the presence of the silver solder, and flows through the cooling return tubes back to the cooling devices 108. In alternate embodiments, other materials may be used instead of silver solder, and the invention is not limited in this regard. As described above, providing cooling to the probes 107 allows heat delivered through the energy delivery devices 192 to be translated further into the tissue without raising the temperature of the tissue immediately adjacent the energy delivery device 192.

As mentioned above, the system 100 of the present invention may further include one or more introducer tubes.

Generally, introducer tubes may include a proximal end, a distal end, and a longitudinal bore extending therebetween. Thus, the introducer tubes (when used) are operable to easily and securely couple with the probe assembly 106. For example, the proximal end of the introducer tubes may be fitted with a connector able to mate reversibly with handle 180 of probe assembly 106. An introducer tube may be used to gain access to a treatment site within a patient's body and a hollow elongate shaft 184 of a probe assembly 106 may be introduced to said treatment site through the longitudinal bore of said introducer tube. Introducer tubes may further include one or more depth markers to enable a user to determine the depth of the distal end of the introducer tube within a patient's body. Additionally, introducer tubes may include one or more radiopaque markers to ensure the correct placement of the introducers when using fluoroscopic guidance.

The system may also include one or more stylets. A stylet may have a beveled tip to facilitate insertion of the one or more introducer tubes into a patient's body. Various forms of stylets are well known in the art and the present invention is not limited to include only one specific form. Further, as described above with respect to the introducer tubes, the stylets may be operable to connect to a power source and may therefore form part of an electrical current impedance monitor. In other embodiments, one or more of the probe assemblies 106 may form part of an electrical current impedance monitor. Thus, the controller 103 may receive impedance measurements from one or more of the stylets, the introducer tubes, and/or the probes 107 and may perform an action, such as alerting a user to an incorrect placement of an energy delivery device 192, based on the impedance measurements.

Figure 3:
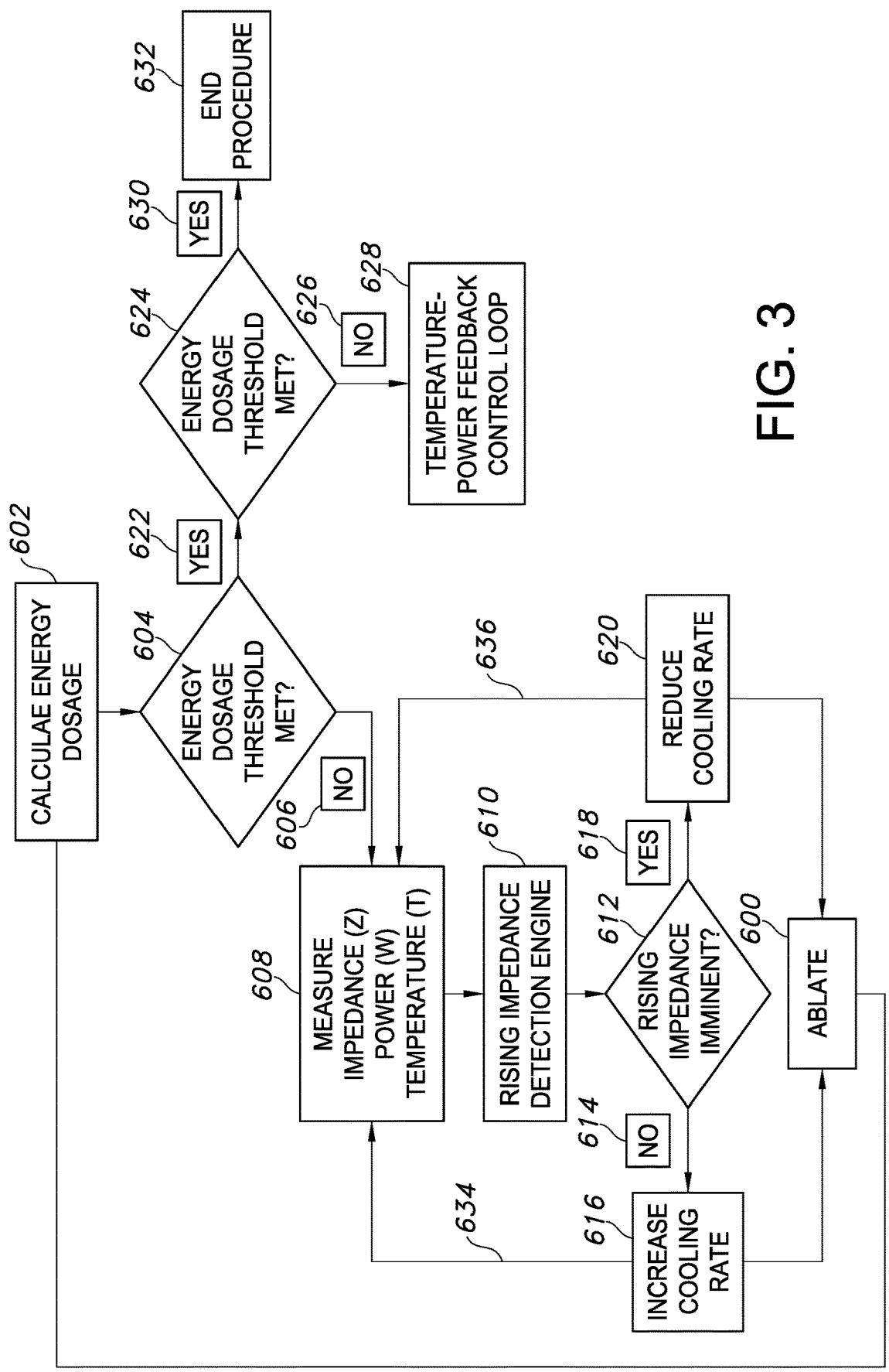
FIG. 3 illustrates a block diagram of one embodiment of a treatment procedure for actively controlling energy delivered to tissue in the patient's body by controlling an amount of energy delivered by the energy delivery devices and a flow rate of the pumps of the pump assembly according to the present disclosure.

FIG. 3 illustrates a block diagram of one embodiment of a control loop for controlling aspects of a treatment procedure. As shown at 600, ablation is initialized. As shown at 602, the energy dosage may be calculated using simple numerical integration techniques. As shown at 604, the calculated energy dosage may then be compared against a preset energy dosage threshold. If the dosage is not satisfied as shown at 606, the procedure continues to 608 to mitigate rising impedance of the internally-cooled probes 107 during the treatment procedure. More specifically, as shown, one or more procedure parameters are monitored while delivering the energy from the generator 102 to the tissue through the energy delivery devices 192. The procedure parameter(s) described herein may include, for example, a temperature of the tissue, an impedance of the tissue, a power demand of the energy delivery device 192, or similar, or combinations thereof. Further, as shown, the procedure parameter(s) 608 may be fed into a rising impedance detection engine 610. As shown at 612, the rising impedance detection engine 610 is configured to determine, e.g. in real-time, whether a rising impedance event is likely to occur in a predetermined time period (i.e. whether the rising impedance event is imminent) based on the received procedure parameter(s) 608. The rising impedance detection engine 610 can then determine a command for the pump assembly 120 based on whether the rising impedance event is likely to occur in the predetermined time period.

If not imminent, as shown at 614, the cooling rate can be increased, e.g. by increasing the pump speed (e.g. via the RPM controllers 125) of the peristaltic pumps 122 as shown at 616. After the cooling rate is increased, the ablation 600 continues. If a rising impedance event is imminent, as shown at 618, the cooling rate can be reduced, e.g. by decreasing the pump speed (e.g. via the RPM controllers 125) of the peristaltic pumps 122 as shown at 620. In other words, in several embodiments, the peristaltic pumps 122 may be independently controlled via their respective RPM controllers 125 to alter the rate of cooling to each electrode 192 of the probes 107. In such embodiments, the power supply 126 of the pump assembly 120 may be decoupled, at least in part, from the generator 102. Further, as shown, the system 550 operates using closed-loop feedback control 634, 636.

Once the energy dosage threshold is satisfied, as shown at 622, the treatment procedure is configured to check if the thermal dosage threshold has been satisfied as shown at 624. If the thermal dosage has not been satisfied, as shown at 626, the treatment procedure proceeds through the independent temperature-power feedback control loop as shown at 628. More specifically, in certain embodiments, the amount of energy delivered through the energy delivery device 192 may be controlled by defining a predetermined threshold temperature for treating the tissue, ramping up the temperature of the tissue via the generator 102 through the energy delivery device 192 to the predetermined threshold temperature, and maintaining the temperature of the tissue at the predetermined threshold temperature to create a lesion in the tissue. In such embodiments, the temperature of the tissue may be maintained at the predetermined threshold temperature as a function of at least one of a power ramp rate, an impedance level, an impedance ramp rate, and/or a ratio of impedance to power.

Only when the thermal dosage threshold has been satisfied, as shown at 630, the procedure terminates as shown at 632. Thus, the system and method of the present disclosure provides the unique features of probe(s) with inherently high-power demand (i.e. short thermocouple protrusion), a pump-modulated power algorithm, a preset energy dosage or total average power threshold, and/or a rising impedance detection engine 610.

Following treatment, energy delivery and cooling may be stopped and the probes 107 are removed from the introducers, where used. A fluid such as an antibiotic or contrast agent may be injected through the introducers, followed by removal of the introducers. Alternatively, the distal tips of the probes 107 may be sharp and sufficiently strong to pierce tissue so that introducers may not be required. As mentioned above, positioning the probes 107, and more specifically the energy delivery devices 192, within the patient's body, may be assisted by various means, including but not limited to fluoroscopic imaging, impedance monitoring and tactile feedback. Additionally, some embodiments of this method may include one or more steps of inserting or removing material into a patient's body.

A system of the present invention may be used in various medical procedures where usage of an energy delivery device may prove beneficial. Specifically, the system of the present invention is particularly useful for procedures involving treatment of back pain, including but not limited to treatments of tumors, intervertebral discs, facet joint denervation, sacroiliac joint lesioning or intraosseous (within the bone) treatment procedures. Moreover, the system is particularly useful to strengthen the annulus fibrosus, shrink annular fissures and impede them from progressing, cauterize granulation tissue in annular fissures, and denature pain-causing enzymes in nucleus pulposus tissue that has migrated to annular fissures. Additionally, the system may be operated to treat a herniated or internally disrupted disc with a minimally invasive technique that delivers sufficient energy to the annulus fibrosus to breakdown or cause a change in function of selective nerve structures in the intervertebral disc, modify collagen fibrils with predictable accuracy, treat endplates of a disc, and accurately reduce the volume of intervertebral disc tissue. The system is also useful to coagulate blood vessels and increase the production of heat shock proteins.

Using liquid-cooled probes 107 with an appropriate feedback control system as described herein also contributes to the uniformity of the treatment. The cooling distal tip regions 190 of the probes 107 helps to prevent excessively high temperatures in these regions which may lead to tissue adhering to the probes 107 as well as an increase in the impedance of tissue surrounding the distal tip regions 190 of the probes 107. Thus, by cooling the distal tip regions 190 of the probes 107, higher power can be delivered to tissue with a minimal risk of tissue charring at or immediately surrounding the distal tip regions 190. Delivering higher power to energy delivery devices 192 allows tissue further away from the energy delivery devices 192 to reach a temperature high enough to create a lesion and thus the lesion will not be limited to a region of tissue immediately surrounding the energy delivery devices 192 but will rather extend preferentially from a distal tip region 190 of one probe assembly 106 to the other.

Figure 4:
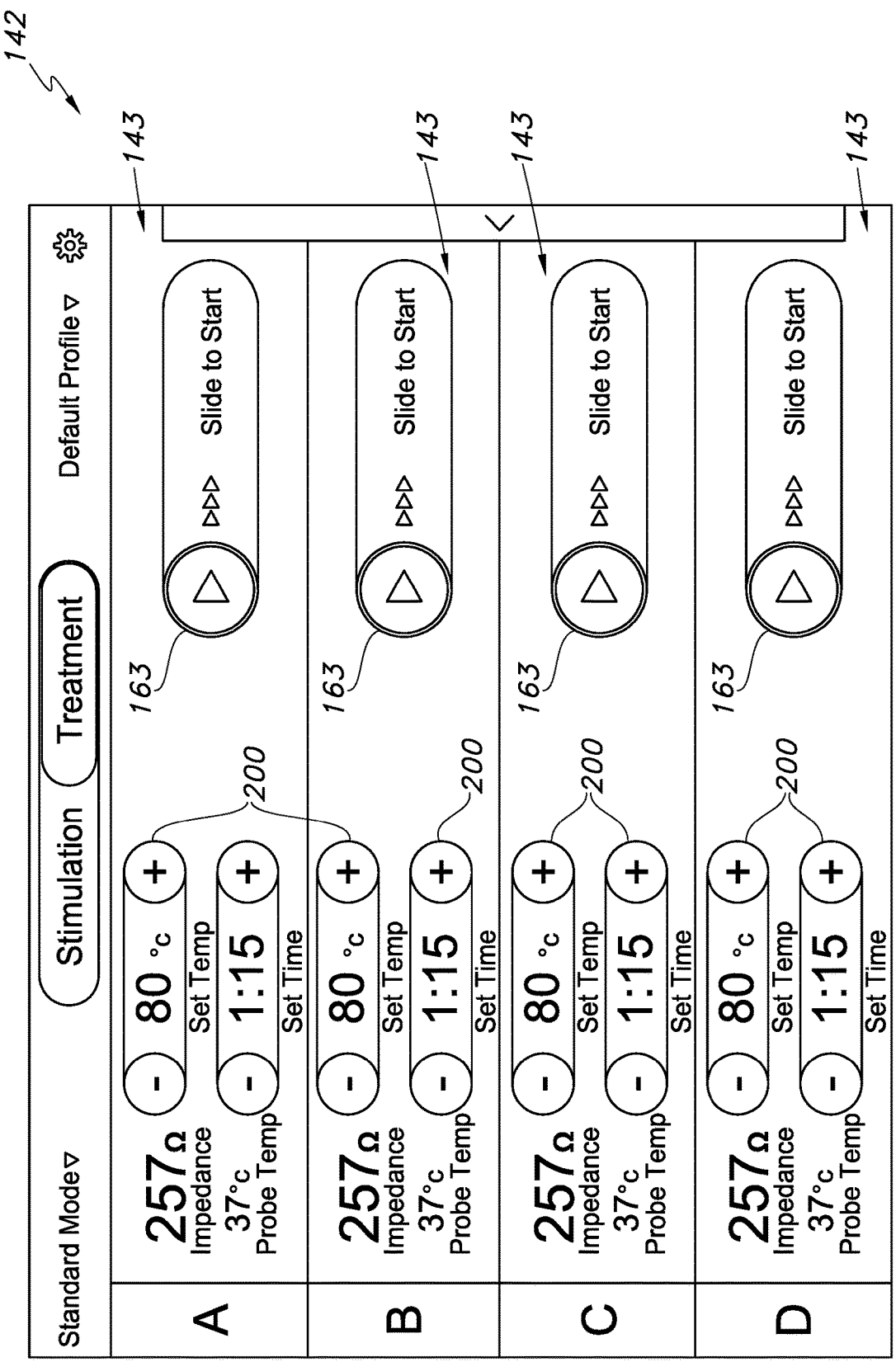
FIG. 4 illustrates a representation of one embodiment of a user interface according to the present disclosure, particularly illustrating a plurality of virtual control objects.
Figure 5:
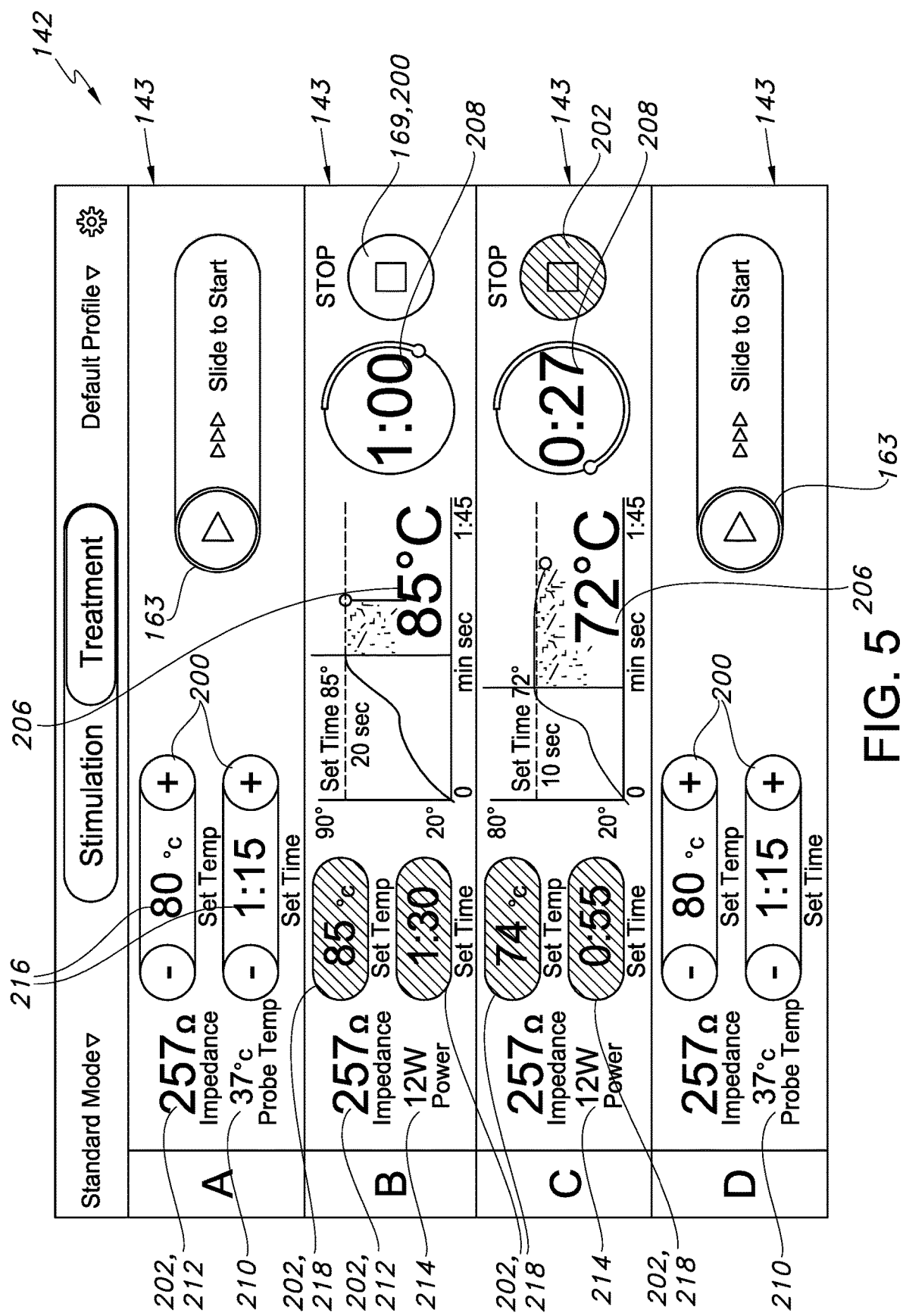
FIG. 5 illustrates a representation of one embodiment of a user interface according to the present disclosure, particularly illustrating virtual control objects and labels, such as non-control labels and non-urgent labels.
Figure 6:
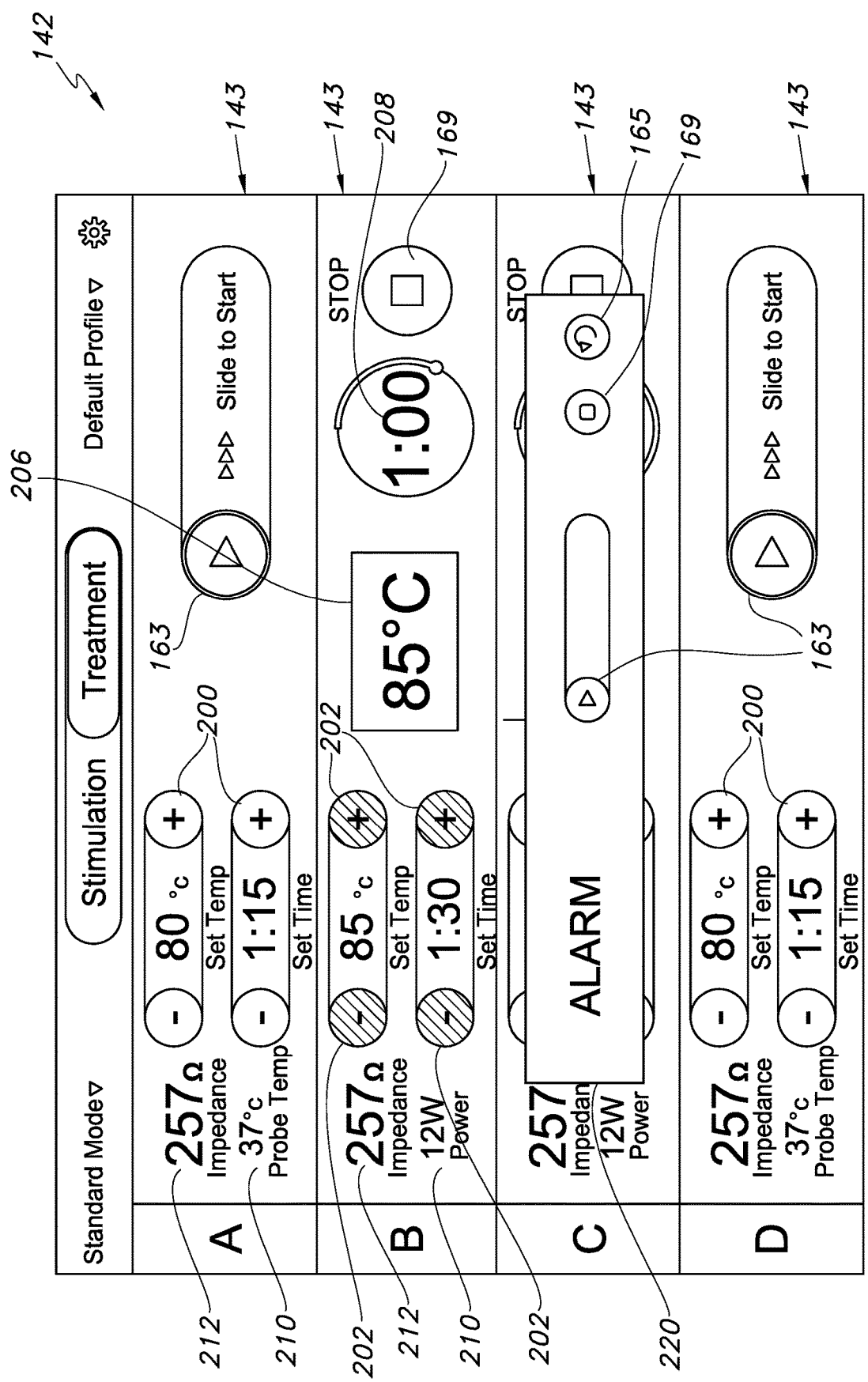
FIG. 6 illustrates a representation of another embodiment of a user interface of a controller of the probe assembly according to the present disclosure, particularly illustrating the user interface with the selective probes actively performing treatment procedures.

Referring to FIGS. 4-6, in some embodiments, the controller 103 may be configured to display one or more virtual control objects in the user interface 142. For example, referring to FIG. 4, a plurality of channel control regions 143 may be defined within the user interface. The user can control the probes 107 individually via the plurality of channel control regions 143. The user interface 142 can enable individual control of the probes 107 by incorporating a "swim lane" concept for each channel. As used herein, the "swim lane" generally refers to the idea of having respective channel control regions 143 associated with the probes 107. Various control objects can be provided within each respective channel control region 143 that allow the user to control aspects of the respective treatment procedures performed with the probes 107. One or more of the channel control regions 143 can include at least one virtual control object, such as a start button, a restart button, a reset button, a stop button, or an independent sliding bar 163 that, upon engagement or selection by the user, is configured to start a treatment procedure for the selected probe 107 from the plurality of probes 107.

In several embodiments, each of the channel control regions 143 may also include one or more individual parameter control objects 200 for allowing the user to control aspects of the treatment procedures. Each individual parameter control object 200 can be used to adjusting the respective associated operating parameter. Example operating parameters include a target temperature, a duration time, target impedance, target power delivery, etc.

More specifically, the controller 103 can be configured to detect a user touch action directed to a virtual control object (e.g., an individual parameter control object 200) that has an associated operating parameter (e.g., target temperature, duration time, etc.). The controller 103 can be configured to perform a control action associated with the treatment procedure (e.g., by adjusting the operating parameter). For example, as illustrated in FIG. 4, the individual parameter control object 200 can include a plus button for increasing the operating parameter and/or a minus button for decreasing the operating parameter. In response to the user touching the plus or minus button, the controller 103 can increase or decrease, respectively, the associated operating parameter.

Referring to FIGS. 5 and 6, in some embodiments, the controller 103 may be configured to convert one or more virtual objects 200 into a non-control label 202 based, at least in part, on a current aspect of the treatment procedure. The controller 103 can be configured to prohibit adjustment of the operating parameter using the non-control label 202 in response to a user touch action that is directed to the non-control label 202.

As an example, the controller 103 may be configured to convert the virtual control object 200 into the non-control label 202 when adjusting the operating parameter associated with the virtual control object 200 would be unsafe for the patient. For example, in some circumstances it may be unsafe to adjust one or more specific operating parameters once the treatment procedure has been initiated or at various stages during the treatment procedure. For instance, the virtual control object 200 can be converted into the non-control label 202 when the treatment procedure associated with the respective control channel 143 is initiated.

As shown in FIG. 4, a treatment procedure has not yet begun with the probe 107 associated with the channel control region 143 labeled "B." In comparison, a treatment procedure is currently being performed with the probe 107 of channel control region labeled 143 "B" in FIG. 5. In FIG. 4, the virtual control objects 200 in channel "B" were configured to adjust two operating parameters (target temperature and duration time). In FIG. 5, these virtual control objects 200 have been converted into non-control labels 202 that display the respective values of the operating parameters. As shown, the plus and minus buttons have been removed, and the non-control label 202 is smaller than the previous virtual control object 200. In addition, the non-control label 202 can be shaded, faded (e.g., "greyed out"), less bold, or displayed in a different color that corresponds with non-control labels. As another example, the plus and minus buttons 200 of the channel control region 143 labeled "B" in FIG. 4 have been converted into non-control labels 202 in the channel control region 143 "B" in FIG. 6.

Referring again to FIGS. 5 and 6, the controller 103 may change a visual characteristic of the non-control label 202 to indicate that to the user that the associated operating parameter can no longer be changed. Example visual characteristics include color, size, brightness, font, location, or contrast. The non-control label 202 can display the associated operating parameter to the user (e.g., real-time values of the operating parameter). In some embodiments, the controller 103 may be further configured to provide the user with a notification in response to a user touch action that is directed to the non-control label 202. The notification can indicate that the associated operating parameter cannot currently be changed, for example, because the treatment procedure has been initiated.

As another example, the controller 103 may be configured to convert the virtual control object into the non-control object in response to a time remaining of the treatment procedure being less than a predetermined time threshold. Referring to FIG. 5, the individual stop button 169 may be converted into a non-control label 202 when the time remaining is less than a predetermined time threshold (e.g., 30 seconds). The non-control label 202 that was previously the individual stop button 169 can have a visual characteristic that is different than the individual stop button 169, including, for example, color, size, brightness, font, location, or contrast. As an example, the non-control label 202 may appear faded or less bold to reflect that the non-control label 202 is no longer responsive to user touch actions. As another example, the sliding bar 163 for starting a treatment procedure may be converted into a non-control label 202 when it is unsafe for the patient to start the treatment procedure, for example, if an operating parameter (e.g., the time duration, target temperature) or a combination of operating parameters fall outside of respective acceptable ranges or fail to meet pre-defined safety criteria.

In some embodiments, one or more virtual control object(s) 200 and one or more non-control label(s) 202 can be displayed within the same control region 143. The non-control label(s) 202 can have visual characteristics that are distinctive from the one or more virtual control object(s) 200 such that the user can quickly and easily discern which portions of the user interface 124 are responsive to user touch actions and/or which operating parameters can currently be adjusted.

In some embodiments, converting the virtual control object 200 into the non-control label 202 can include changing a location of the virtual control object within the user interface 142. For example, non-control labels may generally be grouped in a first region of the user interface 142 and virtual control objects can be grouped in a second region of the user interface 142 to visually distinguish the non-control labels from the virtual control objects. Referring to FIG. 5, the non-control labels 202 can be grouped together towards a left side of the channel control region 143 and virtual control objects 202 can be located towards a right side of the channel control region 143.

Still referring to FIGS. 5 and 6, in some embodiments, the controller 103 can be configured to determine whether an operating parameter of a treatment procedure that is being performed by at least one of the plurality of probes 107 qualifies as contextually important based, at least in part, on a status of the treatment procedure. For example, once the treatment procedure has been initiated, certain operating parameters may qualify as contextually important. In some embodiments, examples may include the time remaining and/or current temperature at the probe 107 (e.g., at the distal tip region 190 of the probe 107). An urgent label 206 can be displayed that indicates the current temperature at the probe 107. Another urgent label 208 can be displayed that indicates the time remaining for the respective treatment procedure. The urgent labels 206, 208 can include real-time values of the respective operating parameters.

In some embodiments, the controller 103 can display non-urgent label(s) that are associated with operating parameters that are determined to be not contextually important. As an example, before starting the treatment procedure, a current probe temperature may not be contextually important. As such, a non-urgent label 210 may be displayed that includes the current probe temperature. However, the current impedance measured at the probe 107 may qualify as contextually important at times before and during the treatment procedure. As such, urgent labels 212 that include the current impedance (e.g., real-time values of the current impedance) may be displayed in channel control regions 143 that correspond with both inactive treatment procedures and with active treatment procedures. As yet another example, during performance of the treatment procedure, the current power level may not qualify as contextually important during an active treatment procedure. As such, a non-urgent label 214 may be displayed that includes the current power level.

It should be understood the whether a given operating parameter qualifies as contextually important can change based on the status of the treatment procedure. For example, before the treatment procedure has been initiated, the controller 103 certain operating parameters may automatically qualify as contextually important (e.g., target temperature, duration time). Once the treatment procedure has been initiated at least one of the current impedance, time remaining, or temperature at a distal tip region 190 of the at least one of the plurality of probes 107 may automatically qualify as contextually important. Once a ramp up period has been successfully completed, a different set of operating parameters than during the ramp up period can automatically qualify as contextually important.

As another example, the target temperature and/or duration time of the procedure may qualify as contextually important before the treatment procedure is initiated, and respective urgent labels 216 may be displayed (for example as shown in channel "A" in FIG. 5). Once the treatment procedure has been initiated (for example as shown in channel "B" in FIG. 5), however, the urgent labels 216 may be converted into non-urgent labels 218. The non-urgent labels 218 may have a visual characteristic that is distinct from the non-urgent label, such as size, color, brightness, font, location, or contrast. For instance, as shown in FIG. 5, the non-urgent labels 218 can be faded or shaded. In other embodiments, the target temperature and/or duration time can be displayed larger as urgent labels 216 before the procedure is started than as non-urgent labels 218 when the treatment procedure is being performed.

In some embodiments, whether a given operational parameter qualifies as contextually important can depend on various other characteristics of the treatment procedure, such as type, mode (e.g., monopolar, bipolar), duration, location of the probes within the patient's body, etc. One or ordinary skill in the art should understand that yet further variations are possible within the scope of this disclosure.

It should also be understood that whether a given operating parameter qualifies as contextually important can change during the treatment procedure. For example, in some embodiments, whether an operating parameter qualifies as contextually important may depend on a comparison between real-time values of the operating parameter and a target value or threshold value associated with the operating parameter. For example, when a monitored operating parameter, such as impedance, deviates from a target impedance value by more than a predetermined amount (or whether rising impedance is likely to occur as described with reference to FIG. 3), the controller 103 may determine that the parameter qualifies as contextually important, whereas the parameter previously did not qualify. As a result, the controller 103 may display an urgent label that includes real-time values of the operating parameter.

In some embodiments, determining whether an operating parameter qualifies as contextually important may be based, at least in part, on whether the information would be important to the physician performing the treatment procedure. As such, in some embodiments, criteria for contextual importance can be set or modified by the physician. The physician generally stands further away from the display screen 123 than a technician or operator. As an example, the physician generally views the display screen 123 from a distance of six or more feet, while the operator generally views the display screen 123 from a distance of one to two feet such that the operator can easily touch the display screen 123 or otherwise engage with controls, for example, to adjust aspects of the treatment procedures. As such, information that is likely to be important to the physician may qualify as contextually important, and, as a result may be displayed using an urgent label such that the urgent label is more visible to the physician than a non-urgent label. For example the urgent label may be bold, larger in size (e.g., 30 point size font or larger) or be displayed in a color with high contrast with have a background color of the user interface 142. In comparison, the non-urgent label may be less bold, smaller (e.g., 10-18 point size font or smaller), and/or displayed with less contrast than the urgent label.

In some embodiments, an alarm and/or warning window 220 may be displayed within a channel control region 143 to indicate an unsatisfactory condition with the associated treatment procedure. For example, the controller 103 may be configured to detect when an operating parameter (e.g., an actual temperature, impedance, power output, etc.) has exceeded a threshold associated with the operating parameter. Depending on the severity of the problem, the controller may automatically stop the treatment procedure and display an alarm or may provide a warning to the user without stopping the treatment procedure. Such alarms and/or warning may be displayed in a color that is distinct from the colors of the channel control regions. Additionally, the channel control region and/or alarm window may be outlined or emphasized in a color that is distinct from the colors of the channel control regions, such as red or white. The alarm and/or warning may include information displayed in the same color as the outline or another color that is distinct from the colors of the channel control regions, such as yellow. In some embodiments, warnings may include text displayed in one color (e.g., yellow), and alarms may include text displayed in a different color (e.g., white).

The alarm window 220 may include a restart button 165 and/or sliding start bar 163 for re-starting the treatment procedure associated with the channel control region 143. The alarm window 220 may also include a stop button 169 for stopping the treatment procedure, if it has not been automatically stopped.

In some embodiments, if all channel control regions become inoperative such that energy is not delivered to the plurality of probes, a "global alarm" may be displayed. The global alarm may include a window that is superimposed over two or more of the channel control regions. Two or more of the channel control regions may be darkened (e.g., faded to black) to emphasize the global alarm. The global alarm may include a message displayed in a color that provides a high contrast with a background of the message (e.g., white text over a black background).

Figure 7:
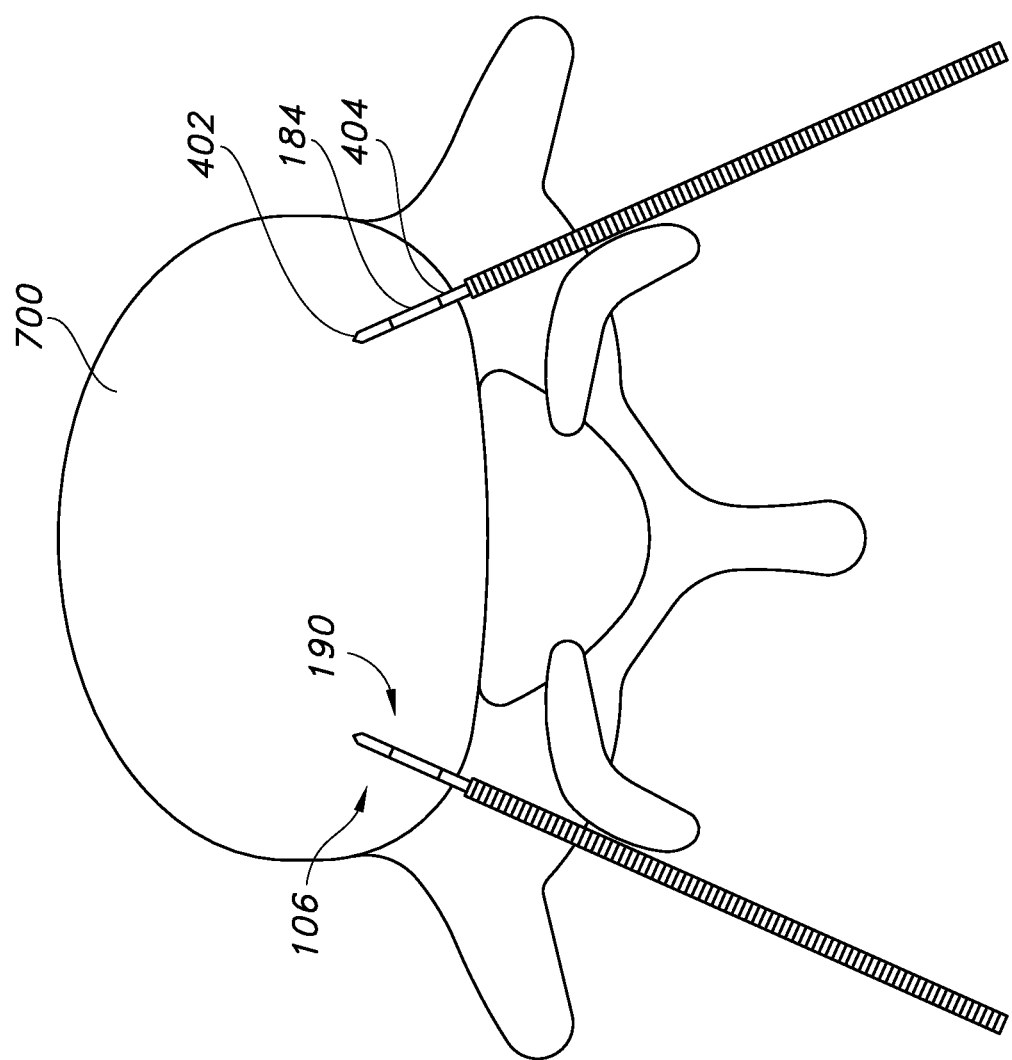
FIG. 7 illustrates two probes placed within an intervertebral disc according to aspects of the present disclosure.

In one embodiment, the plurality of probes 107 may be operated in a bipolar mode. For example, FIG. 7 illustrates one embodiment of two probes 107, wherein the distal tip regions 190 thereof are located within an intervertebral disc 700. In such embodiments, electrical energy is delivered to the probes 107 and this energy is preferentially concentrated therebetween through a region of tissue to be treated (i.e. an area of the intervertebral disc 700). The region of tissue to be treated is thus heated by the energy concentrated between the probes 107. In other embodiments, the probes 107 may be operated in a monopolar mode, in which case an additional grounding pad is required on the surface of a body of a patient, as is known in the art. Any combination of bipolar and monopolar procedures may also be used. It should also be understood that the system may include more than two probe assemblies. For example, in some embodiments, three probe assemblies may be used and the probe assemblies may be operated in a triphasic mode, whereby the phase of the current being supplied differs for each probe assembly.

Figure 8:
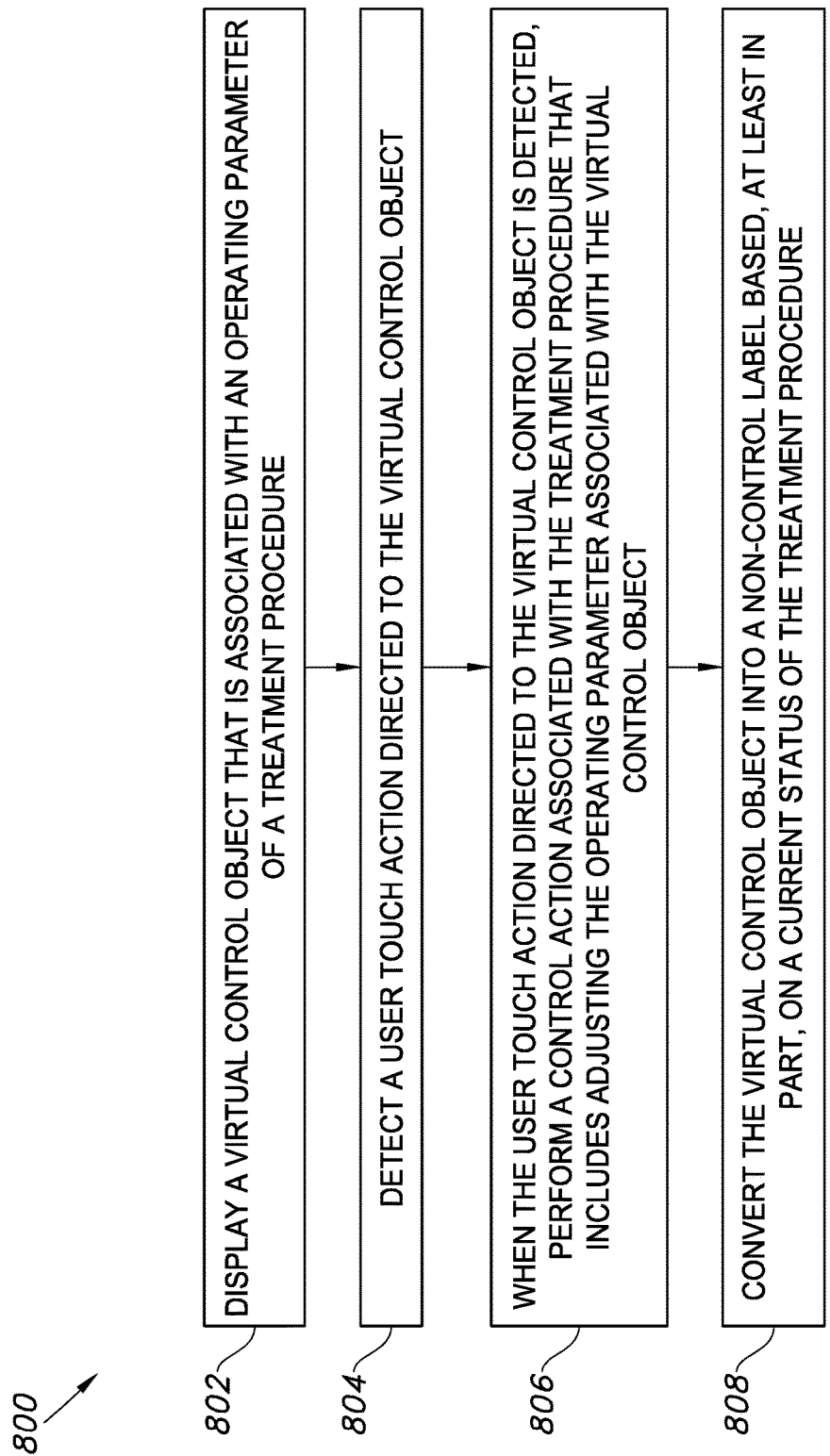
FIG. 8 illustrates a flow diagram of one embodiment of a method for delivering energy to a patient's body using a probe according to the present disclosure.

Referring to FIG. 8, a block diagram of one embodiment of a method 800 for delivering energy to a patient's body, such as an intervertebral disc of the patient's body, for example using the probe assemblies described herein is illustrated. Although FIG. 8 depicts steps performed in a particular order for purposes of illustration and discussion, the methods discussed herein are not limited to any particular order or arrangement. One skilled in the art, using the disclosures provided herein, will appreciate that various steps of the methods disclosed herein can be omitted, rearranged, combined, and/or adapted in various ways without deviating from the scope of the present disclosure.

The method 800 may include, at (802), displaying a virtual control object that is associated with an operating parameter of a treatment procedure in the user interface of the touch-sensitive display screen, for example as described above with reference to FIGS. 4 through 6.

The method may include, at (804), detecting a user touch action directed to the virtual control object, for example as described above with reference to FIGS. 4 through 6. For example, the user may tap, slide, or otherwise engage the virtual control object displayed on the touch-sensitive display screen.

The method may include, at (806), performing a control action associated with the treatment procedure that include adjusting the operating parameter associated with the virtual control object when the user touch action directed to the virtual control object is detected, for example as described above with reference to FIGS. 4 through 6.

The method may include, at (808), converting the virtual control object into a non-control label based, at least in part, on a current status of the treatment procedure, and the controller may be configured to prohibit adjustment of the operating parameter using the non-control label in response to a user touch action that is directed to the non-control label, for example as described above with reference to FIGS. 4 through 6.

Figure 9:
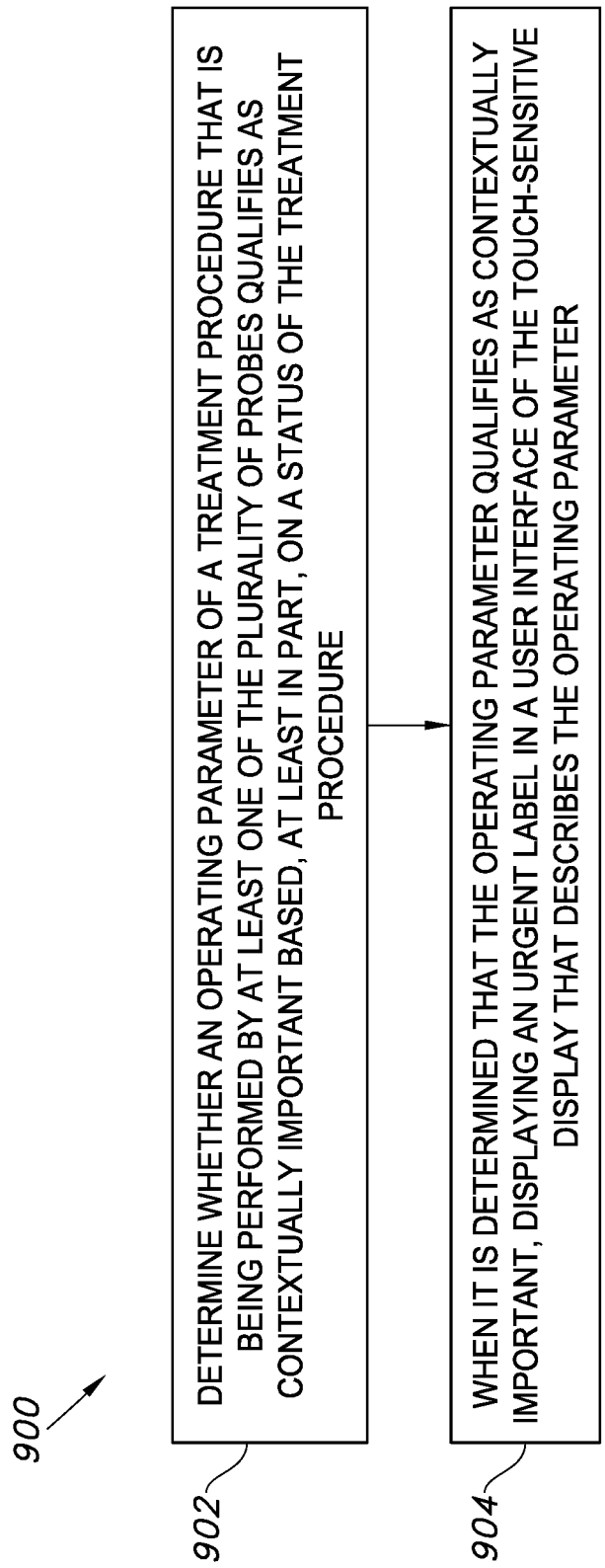
FIG. 9 illustrates a flow diagram of one embodiment of a method for delivering energy to a patient's body using a probe according to the present disclosure.

Referring to FIG. 9, a block diagram of one embodiment of a method 900 for delivering energy to a patient's body, such as an intervertebral disc of the patient's body, for example using the probe assemblies described herein is illustrated.

The method 900 may include, at (902), determining whether an operating parameter of a treatment procedure that is being performed with at least one of the plurality of probes qualifies as contextually important based, at least in part, on a status of the treatment procedure, for example as described above with reference to FIGS. 4 through 6.

The method 900 may include, at (904), displaying an urgent label within a user interface of the touch-sensitive display that includes real-time values of the operating parameter when it is determined that the operating parameter qualifies as contextually important, for example as described above with reference to FIGS. 4 through 6.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A system for delivering energy to a patient's body, the system comprising:
   a probe comprising an elongate member having i) a distal region with an electrically non-conductive outer circumferential portion and a proximal region, and ii) an electrically conductive energy delivery device extending distally from said electrically non-conductive outer circumferential portion for delivering at least one of electrical or radiofrequency energy to the patient's body and having an electrically conductive outer circumferential surface;
   a touch-sensitive display screen; and
   a controller communicatively coupled to the probe and the touch-sensitive display screen, the controller comprising memory and a processor, wherein the memory stores instructions that, when executed by the processor, cause the processor to perform operations comprising:
      displaying a virtual control object within a user interface of the touch-sensitive display screen, the virtual control object being associated with an operating parameter of a treatment procedure performed with the probe;
      detecting a user touch action directed to the virtual control object;
      performing a control action associated with the treatment procedure that comprises adjusting the operating parameter associated with the virtual control object when the user touch action directed to the virtual control object is detected; and
      converting the virtual control object into a non-control label responsive to a determination that i) the treatment procedure has been initiated, or ii) an amount of time remaining in the treatment procedure is less than a predetermined threshold, wherein the controller is configured to prohibit adjustment of the operating parameter using the non-control label in response to a user touch action that is directed to the non-control label.

2. The system of claim 1, wherein the virtual control object is converted into the non-control object further responsive to a determination that iii) adjusting the operating parameter associated with the virtual control object would be unsafe for a patient.

3. The system of claim 1, wherein converting the virtual control object into the non-control label comprises changing a visual characteristic of the virtual control object.

4. The system of claim 3, wherein the visual characteristic comprises at least one of a color, size, brightness, font, location, or contrast of the virtual control object.

5. The system of claim 1, wherein converting the virtual control object into the non-control label comprises changing a location of the virtual control object within the user interface.

6. The system of claim 1, further comprising displaying a second non-control label in the user interface that is separate from the virtual control object and non-control label, and wherein the second non-control label has a visual characteristic that is distinct from the virtual control object.

7. A method for delivering energy to a patient's body using a probe, the method comprising:
   displaying, by one or more control devices, a virtual control object within a user interface of a touch-sensitive display screen, the virtual control object being associated with an operating parameter of a treatment procedure performed by the probe;
   detecting, by the one or more control devices, a user touch action directed to the virtual control object;
   when the user touch action directed to the virtual control object is detected, performing, by the one or more control devices, a control action associated with the treatment procedure that comprises adjusting the operating parameter associated with the virtual control object; and
   converting, by the one or more control devices, the virtual control object into a non-control label responsive to a determination that i) the treatment procedure has been initiated, or ii) an amount of time remaining in the treatment procedure is less than a predetermined threshold, wherein the controller is configured to prohibit adjustment of the operating parameter using the non-control label in response to a user touch action that is directed to the non-control label.

8. The method of claim 7, wherein the virtual control object is converted into the non-control label further responsive to a determination that iii) adjusting the operating parameter associated with the virtual control object would be unsafe for a patient.

9. The method of claim 8, wherein converting the virtual control object into the non-control label comprises changing a visual characteristic of the virtual control object.

10. The method of claim 8, further comprising displaying a second non-control label in the user interface that is separate from the virtual control object and non-control label, and wherein the second non-control label has a visual characteristic that is distinct from the virtual control object.

11. A system for delivering energy to a patient's body, the system comprising:
   a plurality of probes each comprising an elongate member having a distal region with an electrically non-conductive outer circumferential portion and a proximal region, each of the plurality of probes further comprising an electrically conductive energy delivery device extending distally from said electrically non-conductive outer circumferential portion for delivering at least one of electrical or radiofrequency energy to the patient's body and having an electrically conductive outer circumferential surface;
   a touch-sensitive display screen; and
   a controller communicatively coupled to each of the plurality of probes and the touch-sensitive display screen, the controller comprising memory, a processor, and, the memory storing instructions that, when executed by the processor, cause the processor to perform operations, the operations comprising:
      displaying, within a user interface of the touch-sensitive display, a plurality of channel control regions each corresponding to one of the plurality of probes, wherein each of the plurality of channel control regions indicates real-time values for a first set of operating parameters of a treatment procedure that is being performed corresponding ones of the plurality of probes;
      identifying at least one additional operating parameter that is contextually important to the treatment procedure based on a status of the treatment procedure; and responsive to identifying the at least one additional operating parameter that is contextually important, modifying the user interface to replace the displayed real-time values of at least one of the first set of operating parameters with real-time values of the at least one additional operating parameter.

12. The system of claim 11, wherein the at least one additional operating parameter that is contextually important is visually emphasized with at least one of a color, size, contrast, or brightness, as compared with surrounding portions of the user interface.

13. The system of claim 11, wherein the at least one additional operating parameter that is contextually important has a visual characteristic that is distinct from the remaining ones of the first set of operating parameters.

14. The system of claim 13, wherein the visual characteristic comprises at least one of size, color, brightness, font, location, or contrast.

15. The system of claim 11, wherein the operations further comprise removing or replacing the at least one additional operating parameter when it is determined that the at least one additional operating parameter no longer qualifies as contextually important based on a current phase of the treatment procedure.

16. The system of claim 11, wherein the at least one additional operating parameter comprises at least one of impedance, time remaining, or a temperature at a distal region of the at least one of the plurality of probes, and wherein the at least one additional operating parameter qualifies as contextually important when the status of the treatment procedure comprises actively delivering at least one of electrical or radiofrequency energy to the patient's body.

17. The system of claim 11, wherein the at least one additional operating parameter comprises at least one of a target temperature for a distal region of the at least one of the plurality of probes, a duration time for the treatment procedure, or a power level of the treatment procedure, and wherein the at least one additional operating parameter fails to qualify as contextually important when the status of the treatment procedure comprises actively delivering at least one of electrical or radiofrequency energy to the patient's body.

18. The system of claim 11, wherein the at least one additional operating parameter comprises a temperature at a distal region of the at least one of the plurality of probes, and wherein the at least one additional operating parameter fails to qualify as contextually important when the treatment procedure has not been initiated.

* * * * *